United States Patent
Hasegawa et al.

(10) Patent No.: US 7,946,989 B2
(45) Date of Patent: May 24, 2011

(54) ULTRASONIC DIAGNOSING APPARATUS AND ULTRASONIC IMAGE DISPLAY METHOD

(75) Inventors: Kinya Hasegawa, Kanagawa (JP); Masahiro Hamamoto, Tokyo (JP)

(73) Assignee: Panasonic Corporation, Osaka (JP)

( * ) Notice: Subject to any disclaimer, the term of this patent is extended or adjusted under 35 U.S.C. 154(b) by 417 days.

(21) Appl. No.: 11/568,877

(22) PCT Filed: May 13, 2005

(86) PCT No.: PCT/JP2005/008808
§ 371 (c)(1), (2), (4) Date: Mar. 9, 2007

(87) PCT Pub. No.: WO2005/110237
PCT Pub. Date: Nov. 24, 2005

(65) Prior Publication Data
US 2007/0249937 A1    Oct. 25, 2007

(30) Foreign Application Priority Data
May 14, 2004    (JP) .................................. 2004-145710

(51) Int. Cl.
*A61B 8/00*    (2006.01)
(52) U.S. Cl. ...................................................... 600/443
(58) Field of Classification Search .................... 600/443
See application file for complete search history.

(56) References Cited

U.S. PATENT DOCUMENTS

| | | | |
|---|---|---|---|
| 5,456,256 A * | 10/1995 | Schneider et al. | ............ 600/445 |
| 6,248,074 B1 | 6/2001 | Ohno et al. | |
| 2004/0081340 A1 | 4/2004 | Hashimoto | |
| 2004/0087854 A1 | 5/2004 | Ueda | |
| 2004/0249287 A1 | 12/2004 | Kawashima et al. | |
| 2005/0090743 A1* | 4/2005 | Kawashima et al. | ......... 600/443 |

FOREIGN PATENT DOCUMENTS

| | | | |
|---|---|---|---|
| JP | 2001-170057 | | 6/2001 |
| JP | 2001170057 | * | 6/2001 |
| JP | 2002-078710 | | 3/2002 |
| JP | 2002-78710 | | 3/2002 |
| JP | 2003-325513 | | 11/2003 |
| JP | 2004-049426 | * | 2/2004 |
| JP | 2004-49426 | | 2/2004 |

OTHER PUBLICATIONS

Chinese Office Action with English translation.

* cited by examiner

*Primary Examiner* — Tse Chen
*Assistant Examiner* — Hien Nguyen
(74) *Attorney, Agent, or Firm* — Pearne & Gordon LLP (57) ABSTRACT

A technique for displaying an ultrasonic three-dimensional image and its tomographic image at the same time is disclosed. According to the technique, it is provided with: a transmitting/receiving circuit 111 for carrying out a transmitting/receiving control of ultrasonic waves; a three-dimensional processing unit 120 for forming a three-dimensional image from an ultrasonic reception signal received by the transmitting/receiving circuit; an image processing circuit 115 for converting the tomographic image and the three-dimensional image into a display format; and the like. The three-dimensional processing unit is composed of: an angle detecting circuit 121 for generating an angle information of a high resolution from two encoder signals of a rotation and an oscillation; and a high speed operation processing circuit 122 for carrying out processes of generation, treatment and cut of a three-dimensional image data, and the like.

13 Claims, 12 Drawing Sheets

PRIOR ART

ULTRASONIC DIAGNOSING APPARATUS AND ULTRASONIC IMAGE DISPLAY METHOD

TECHNICAL FIELD

The present invention relates to an ultrasonic diagnosing apparatus and an ultrasonic image display method that can display a three-dimensional image.

BACKGROUND ART

Figure 12:
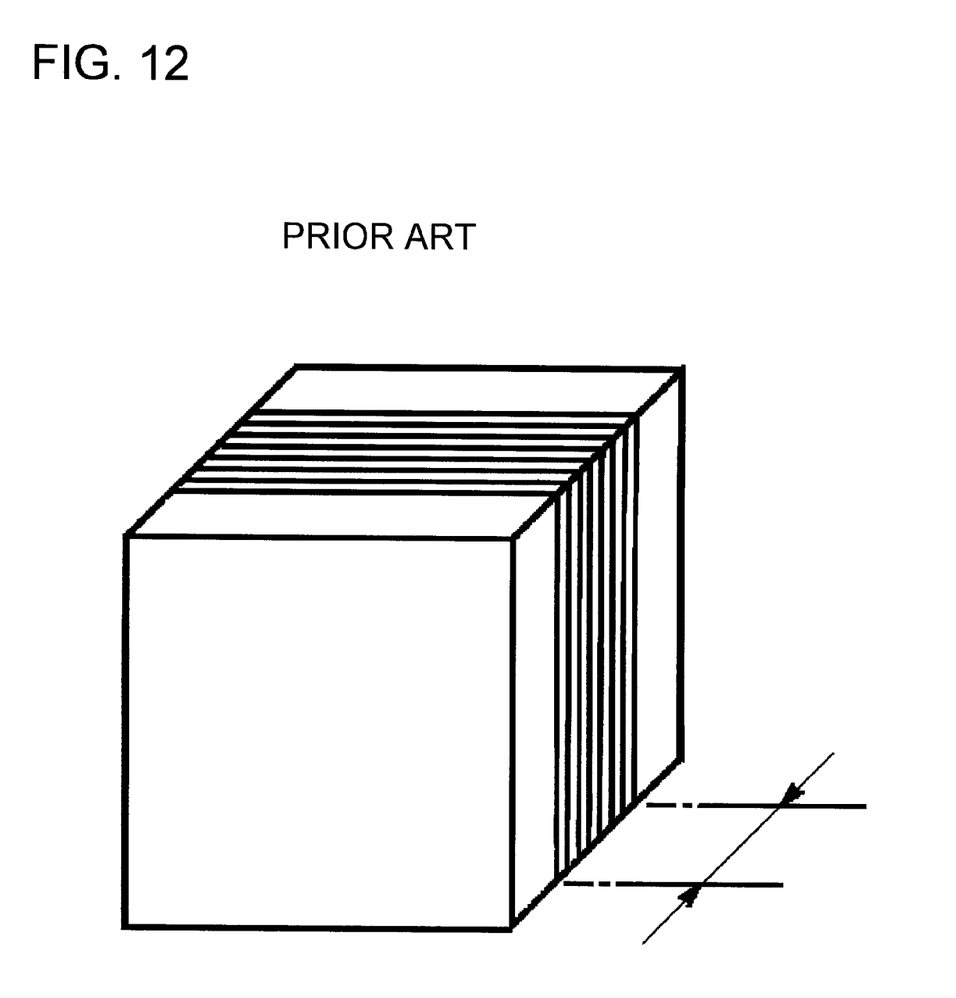
[FIG. 12] is an explanation view of a prior art.

A conventional ultrasonic diagnosing apparatus is designed, as shown in FIG. 12, so as to transmit and receive ultrasonic waves and consequently form a three-dimensional image and specify a predetermined range for the formed three-dimensional capture space and then display a plurality of tomographic images at a uniform division in its range (for example, refer to the following patent document 1).

Patent Document 1: Japanese Patent Application Publication (JP-P 2001-170057A) (Pages 5 to 7)

However, the above-mentioned conventional ultrasonic diagnosing apparatus has a problem that, when the plurality of tomographic images are displaced for the three-dimensional image, the predetermined range is specified for the three-dimensional capture space, and the tomographic images are only displayed at the uniform division in its range, and an angle of a division direction and a division rage cannot be arbitrarily changed and there is no free degree in displaying the diagnosis image.

DISCLOSURE OF THE INVENTION

The present invention is proposed to solve the foregoing conventional problems and has an object to provide an ultrasonic diagnosing apparatus that can display a three-dimensional image at real time and division-display any tomographic image of this three-dimensional image and consequently improve a diagnosis precision.

The ultrasonic diagnosing apparatus of the present invention comprises: connecting means that can connect a probe having an ultrasonic transducer unit to transmit and receive ultrasonic waves; transmitting/receiving means for supplying an ultrasonic signal to the ultrasonic transducer unit and carrying out a reception process of the ultrasonic signal received by the ultrasonic transducer unit; an image memory for storing the received and processed ultrasonic signal as an image data; and three-dimensional operating means for forming the three-dimensional image from the image data stored in the image memory at real time, wherein the three-dimensional operating means is designed so as to cut and division-display a plurality of tomographic images of the three-dimensional image at any set positions and angles within a three-dimensional display range including the three-dimensional image.

With this configuration, the plurality of tomographic images of any portion in the three-dimensional image can be displayed, and the situation inside a specimen can be easily grasped, thereby improving the precision and efficiency in an ultrasonic diagnosis.

Also, an ultrasonic diagnosing apparatus comprises: connecting means that can connect a probe having an ultrasonic transducer unit to transmit and receive ultrasonic waves, a rotating motor and an oscillating motor; transmitting/receiving means for supplying an ultrasonic signal to the ultrasonic transducer unit and carrying out a reception process of the ultrasonic signal received by the ultrasonic transducer unit; rotation control means for carrying out a rotation control of the rotating motor; oscillating control means for carrying out an oscillating control of the oscillating motor; an image memory for storing the received and processed ultrasonic signal as an image data; and three-dimensional operating means for forming a three-dimensional image from the image data stored in the image memory, wherein the three-dimensional operating means is designed so as to cut and division-display a plurality of tomographic images of the three-dimensional image at any set positions and angles within a three-dimensional display range including the three-dimensional image.

With this configuration, in a mechanism sector probe, the plurality of tomographic images of any portion in the three-dimensional image can be displayed, and the situation inside the specimen can be easily grasped, thereby improving the precision and efficiency in the ultrasonic diagnosis.

Also, the ultrasonic diagnosing apparatus of the present invention is designed so as to display the plurality of tomographic images and the three-dimensional image at the same time.

With this configuration, the three-dimensional image and the tomographic image can be observed at the same time, and the diagnosis precision and efficiency can be improved.

Also, the ultrasonic diagnosing apparatus of the present invention is designed such that a position of the tomographic image division-displayed within the three-dimensional display range is displayed on the three-dimensional image.

With this configuration, the plurality of tomographic images and the three-dimensional image can be related and observed at the same time, and the diagnosis precision and efficiency can be improved.

Also, the ultrasonic diagnosing apparatus of the present invention is designed such that between a position of an upper limit and a position of a lower limit to be division-displayed as the tomographic images within the three-dimensional display range, the tomographic images are cut and displayed at a preliminarily specified interval.

With this configuration, the plurality of tomographic images can be observed at a necessary portion, and the diagnosis precision and efficiency can be improved.

Also, the ultrasonic diagnosing apparatus of the present invention is designed so as to comprise means for selecting the division-displayed tomographic image, wherein the selected tomographic image is enlargement-displayed.

With this configuration, among the plurality of tomographic images, the portion desired to be observed in detail can be enlargement-displayed, thereby improving the diagnosis precision and efficiency.

Also, the ultrasonic diagnosing apparatus of the present invention is designed so as to comprise means for selecting the position of the tomographic image displayed on the three-dimensional image, wherein the tomographic image of the selected position is enlargement-displayed.

With this configuration, among the plurality of tomographic images, the portion desired to be observed in detail can be enlargement-displayed, thereby improving the diagnosis precision and efficiency.

Also, an ultrasonic image display method of the present invention is designed to carry out a reception process of an ultrasonic signal received from a probe having an ultrasonic transducer unit, and store the received and processed ultrasonic signal as an image data in an image memory, and when forming a three-dimensional image from the image data stored in the image memory, cut and division-display a plurality of tomographic images of the three-dimensional image at any set positions and angles within a three-dimensional display range including the three-dimensional image.

With this configuration, the plurality of tomographic images of any portion in the three-dimensional image can be displayed, and the situation inside the specimen can be easily grasped, thereby improving the precision and efficiency in the ultrasonic diagnosis.

The present invention comprises the three-dimensional operating means for forming the three-dimensional image from the image data obtained by transmitting and receiving the ultrasonic wave to and from an organism, and this three-dimensional operating means displays the three-dimensional image at real time and cuts and division-displays the plurality of tomographic images of the three-dimensional image at any set positions and angles within the three-dimensional display ranges including this three-dimensional image. Thus, the plurality of tomographic images of any portion in the three-dimensional image can be displayed, and the situation inside the specimen can be easily grasped, thereby improving the precision and efficiency in the ultrasonic diagnosis.

BEST MODE FOR CARRYING OUT THE INVENTION

An ultrasonic diagnosing apparatus of an embodiment of the present invention will be described below by using the drawings. This embodiment is noted with regard to the ultrasonic diagnosing apparatus in which a three-dimensional ultrasonic probe of a mechanical sector type (hereafter, merely referred to as [Three-Dimensional Probe], [Probe]) is connected, and through this probe, ultrasonic waves is transmitted and received, and an image display including a three-dimensional image is carried out.

Figure 1A:
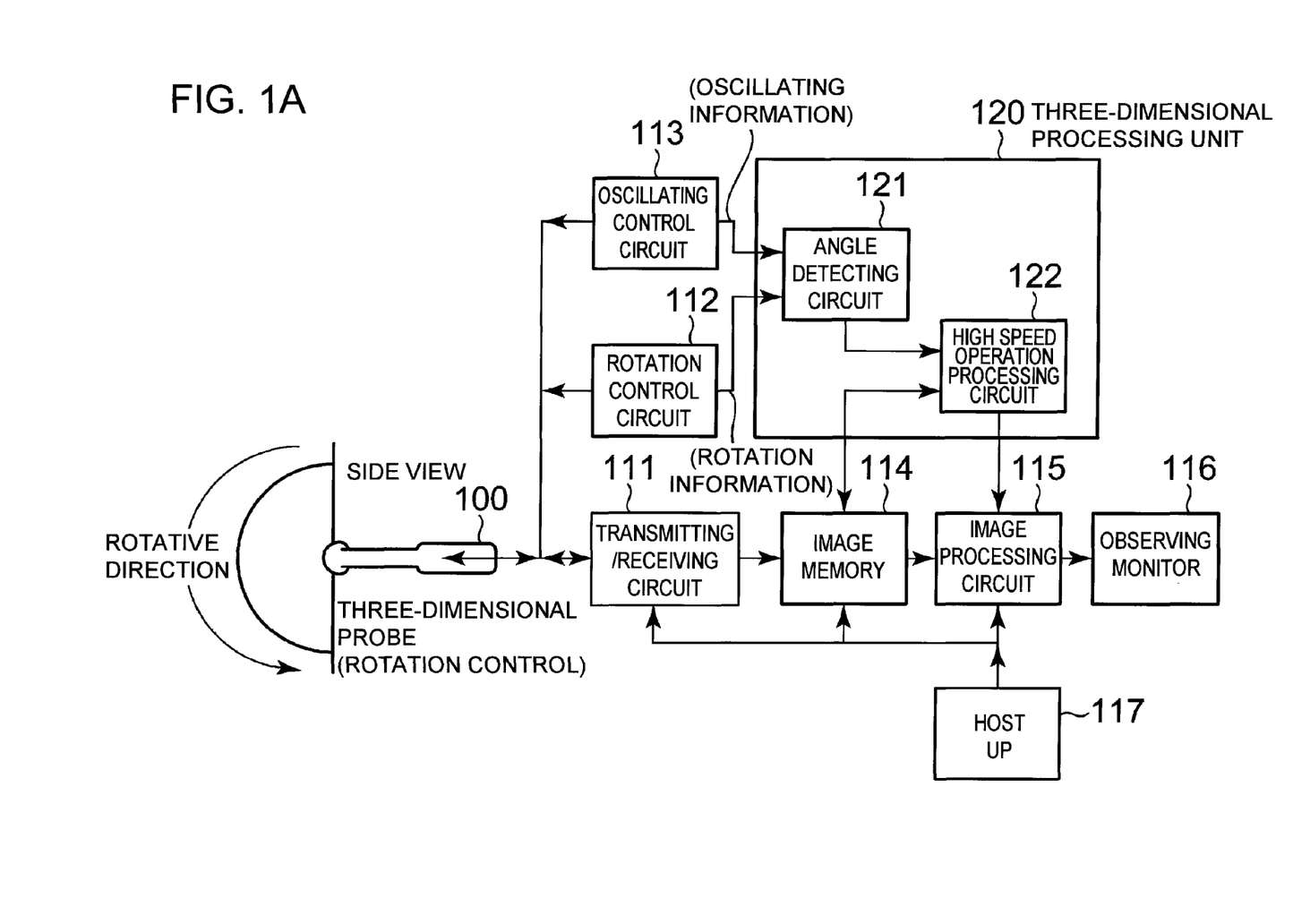
[FIG. 1A] is a block diagram of an ultrasonic diagnosing apparatus in an embodiment of the present invention.
Figure 1B:
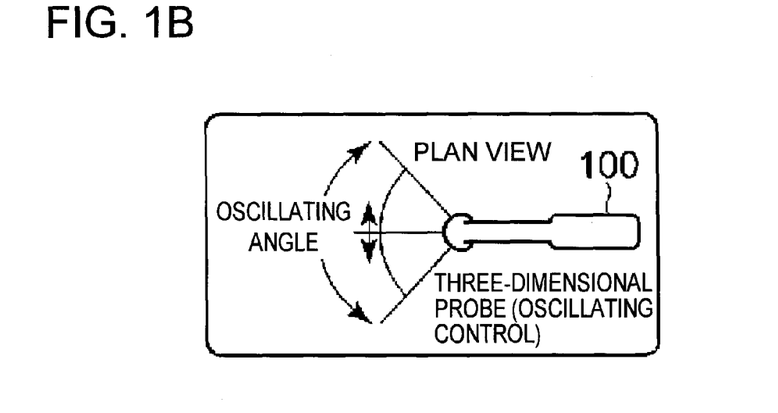
[FIG. 1B] is a plan view of a three-dimensional probe shown in FIG. 1A.

As shown in FIG. 1A and FIG. 1B, the ultrasonic diagnosing apparatus in the embodiment of the present invention is provided with: a probe 100 that has an ultrasonic transducer unit for transmitting/receiving the ultrasonic wave while it is rotated and oscillated; a probe connector (not shown) to which this probe 100 can be connected; a transmitting/receiving circuit 111 for carrying out a transmitting/receiving control of the ultrasonic wave; a rotation control circuit 112 for stabilizing a speed of a rotation while receiving a rotation encoder signal of the probe; an oscillating control circuit 113 for controlling a speed and an angle of the oscillation while receiving an oscillation encoder signal; an image memory 114 for storing a tomographic image data including a three-dimensional image data; a three-dimensional processing unit 120 for forming the three-dimensional image from the ultrasonic reception signal received by the transmitting/receiving circuit; an image processing circuit 115 for converting into a format to display the tomographic image and the three-dimensional image; an observing monitor 116 for displaying the ultrasonic image into which the display format is converted and the like; and a host up 117 for controlling the entire system. The three-dimensional processing unit 120 is composed of: an angle detecting circuit 121 for generating an angle information of a high resolution from the two encoder signals of the rotation and the oscillation; and a high speed operation processing circuit 122 for carrying out the processes of the generation, the treatment and the cut of the three-dimensional image data, and the like.

Also, this contains input devices (not shown), such as a trackball, a keyboard, a sound input circuit and the like, in order to carry out an operation and a setting.

By the way, as for the probe, FIG. 1A is a side view showing a rotative direction when the probe 100 is rotated, and FIG. 1B is a plan view showing an oscillation range when the probe 100 is oscillated.

Figure 2:
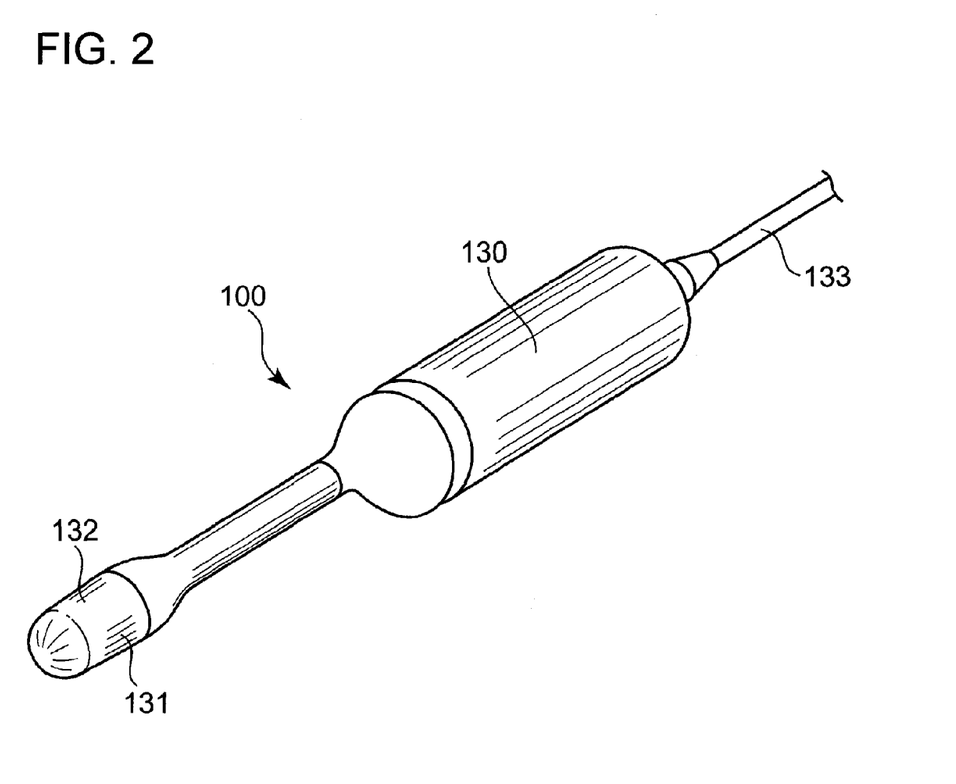
[FIG. 2] is a perspective view of a mechanical sector probe in the embodiment of the present invention.
Figure 3:
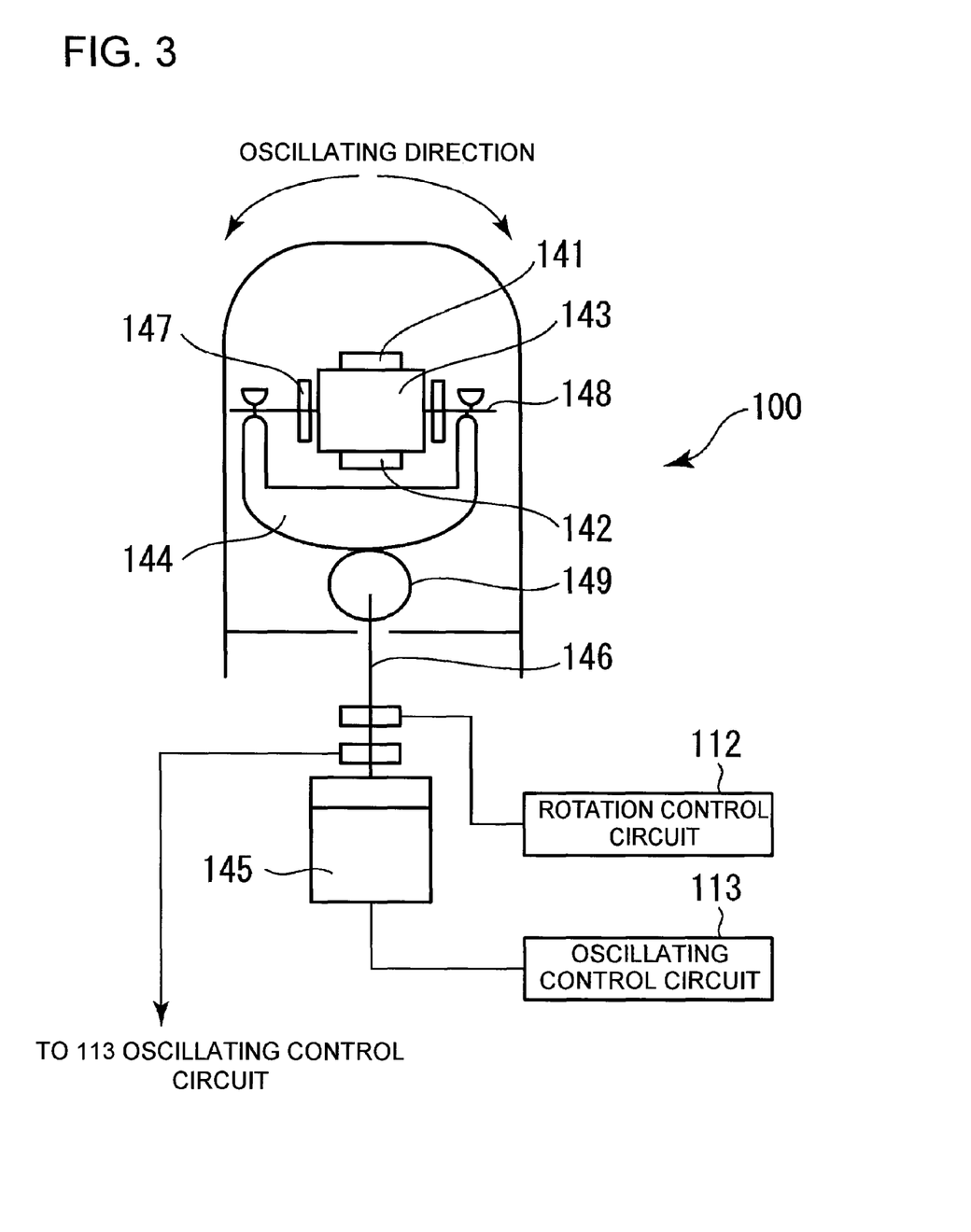
[FIG. 3] is a configuration view of the mechanical sector probe in the embodiment of the present invention.

Here, the configuration of the probe 100 is explained by using FIG. 2 and FIG. 3.

In FIG. 2, 130 indicates a handle unit, and a relaying electronic circuit substrate, such as an oscillating motor and the like, is built therein. 131 indicates a tip unit of the ultrasonic probe (hereafter, merely referred to as [Tip Unit]), and a window case 132 made of a window material having an ultrasonic transmission characteristic is attached to the tip, and a driving motor, an ultrasonic transducer unit and the like are built therein. The ultrasonic probe is connected through a cable 133 to a main body. A tip unit 131 has a cylindrical smooth streamline shape so as to be easily inserted into the body. This cable 133 is the cable to connect an input/output line (I/O line) for connecting the ultrasonic transducer unit and the ultrasonic diagnosing apparatus main body, an electric control line for drive-controlling the driving motor and an oscillating motor, a signal line for an encoder and the like, a signal line for impact detection and the like, to the ultrasonic diagnosing apparatus main body, and it is protected with a cable coating, and only the input/output line is shielded and grounded at both ends of an ultrasonic transducer unit side and an ultrasonic diagnosing apparatus side.

Also, in FIG. 3, a rotating motor 143 for rotation-driving ultrasonic transducer units 141, 142, a rotation shaft 148 serving as its rotation shaft, and a base housing 144 for supporting the rotating motor 143 are built in the tip of the probe 100. The handle unit of the ultrasonic probe is composed of an oscillating motor 145 for oscillating the base housing 144 and a handle shaft 146.

The ultrasonic transducer units 141, 142 are mounted onto the outer circumference of the rotating unit of the rotating motor 143, and with respect to the rotation shaft, the ultrasonic transducer units 141, 142 emit ultrasonic beam to a radial direction.

Figure 4:
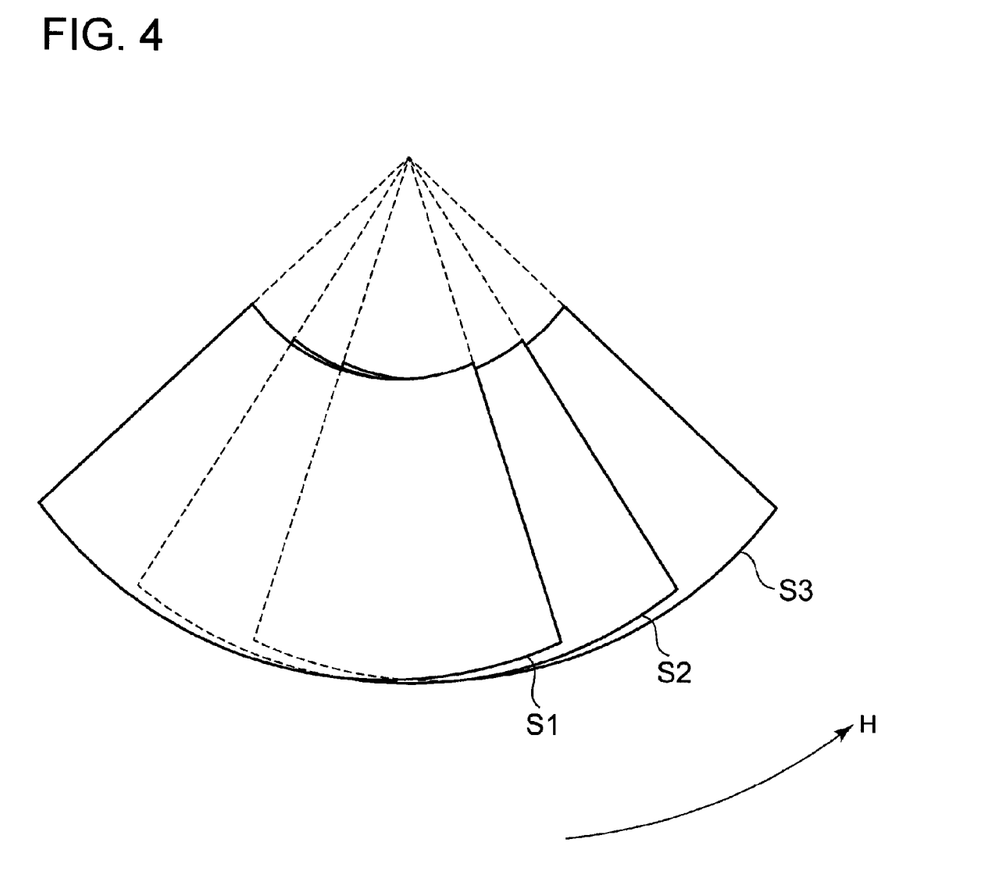
[FIG. 4] is a conceptual view when a three-dimensional image is formed from a two-dimensional image.

Also, the case of forming the conventional two-dimensional image has one shaft. However, the case of the probe 100 in this embodiment has two shafts, and one is the rotation shaft 148 for rotating the ultrasonic transducer units 141, 142, and the other is an oscillating shaft 149. With the rotation shaft 148 as a center, while the ultrasonic transducer units 141, 142 are rotated, the ultrasonic wave is transmitted and received, thereby forming the two-dimensional image as shown by S1 of FIG. 4, and with the oscillating shaft 149 as a center, the base housing 144 for supporting the rotating motor 143 is oscillated in an H-direction of FIG. 4, and the two-dimensional images of S1, S2 and S3 are formed in rotation, thereby drawing the three-dimensional image.

The operation of the ultrasonic diagnosing apparatus in this embodiment of the present invention will be described below.

An ultrasonic pulse generated by a transmission pulse generating circuit (not shown) in the transmitting/receiving circuit 111 is transmitted at a predetermined interval from the ultrasonic transducer units 141 or 142 of the probe 100, and the ultrasonic pulse reflected by a tissue of an organism and the like is received by the ultrasonic transducer units 141 or 142. At this time, while the rotation control circuit 112 rotations the rotating motor 143, the ultrasonic transducer units 141 or 142 carries out the transmission/reception, and the data to form the two-dimensional image indicated in S1 is consequently obtained. The receiving circuit of the transmitting/receiving circuit 111 performs the receiving process on this received ultrasonic reception signal, which is stored in the image memory 114.

Simultaneously, the oscillating control circuit 113 rotations the oscillating motor 145, and sequentially receives the data to form the two-dimensional image, and then writes to the image memory 114. The high speed operation processing circuit 122 in the three-dimensional processing unit 120 carries out a polar coordinates conversion and prepares the three-dimensional data. This three-dimensional data is stored in the image memory 114 or sequentially displayed through the image processing circuit 115 on the observing monitor 116.

At this time, when the two-dimensional image for each screen is formed, the control is executed such that in response to an oscillating motor control timing, the two-dimensional is obtained for one screen. Thus, the two-dimensional image can be obtained at a constant interval in synchronization with the oscillation of the motor. Hence, a geometric precision of the three-dimensional image can be improved.

In the three-dimensional data preparation, the two-dimensional image is captured, and an operating process such as an addition and the like is carried out, and the image where the three-dimensional data is projected to a plan surface is prepared. Then, the three-dimensional image is displayed at real time, or formed in the image memory, and then displayed.

The three-dimensional image is prepared and displayed for each one way oscillation of the oscillating motor 145 in the probe 100. In accordance with a voxel data after the coordinate conversion from the polar coordinates to an orthogonal coordinate, the three-dimensional image is formed. Thus, the three-dimensional image without any distortion can be displayed.

By the way, when the three-dimensional image is formed, the three-dimensional image may be formed for each reciprocating oscillation without being formed for each one way oscillation. Such operation enables the display precision of the three-dimensional image to be made higher.

The image processing circuit 115 converts the three-dimensional data into an image format so that it can be displayed as the three-dimensional image on the observing monitor 116.

The host up 117 controls those series of the processes.

As for the three-dimensional data stored in the image memory 114, the high speed operation processing circuit 122 can read the data at any position.

The operation with regard to a so-called multi-slice display will be described below.

Figure 5:
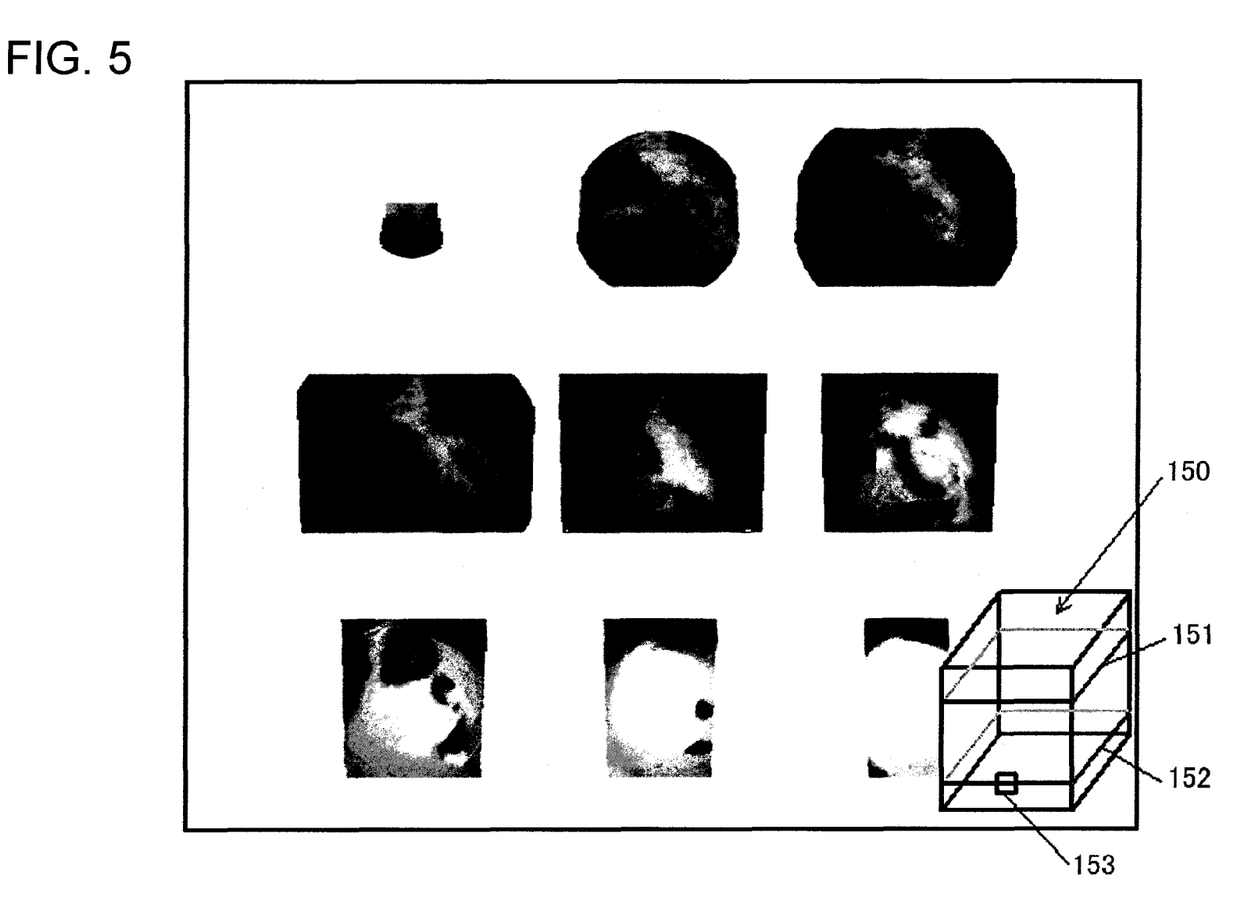
[FIG. 5] is a view showing one example of a multi-slice display.
Figure 6:
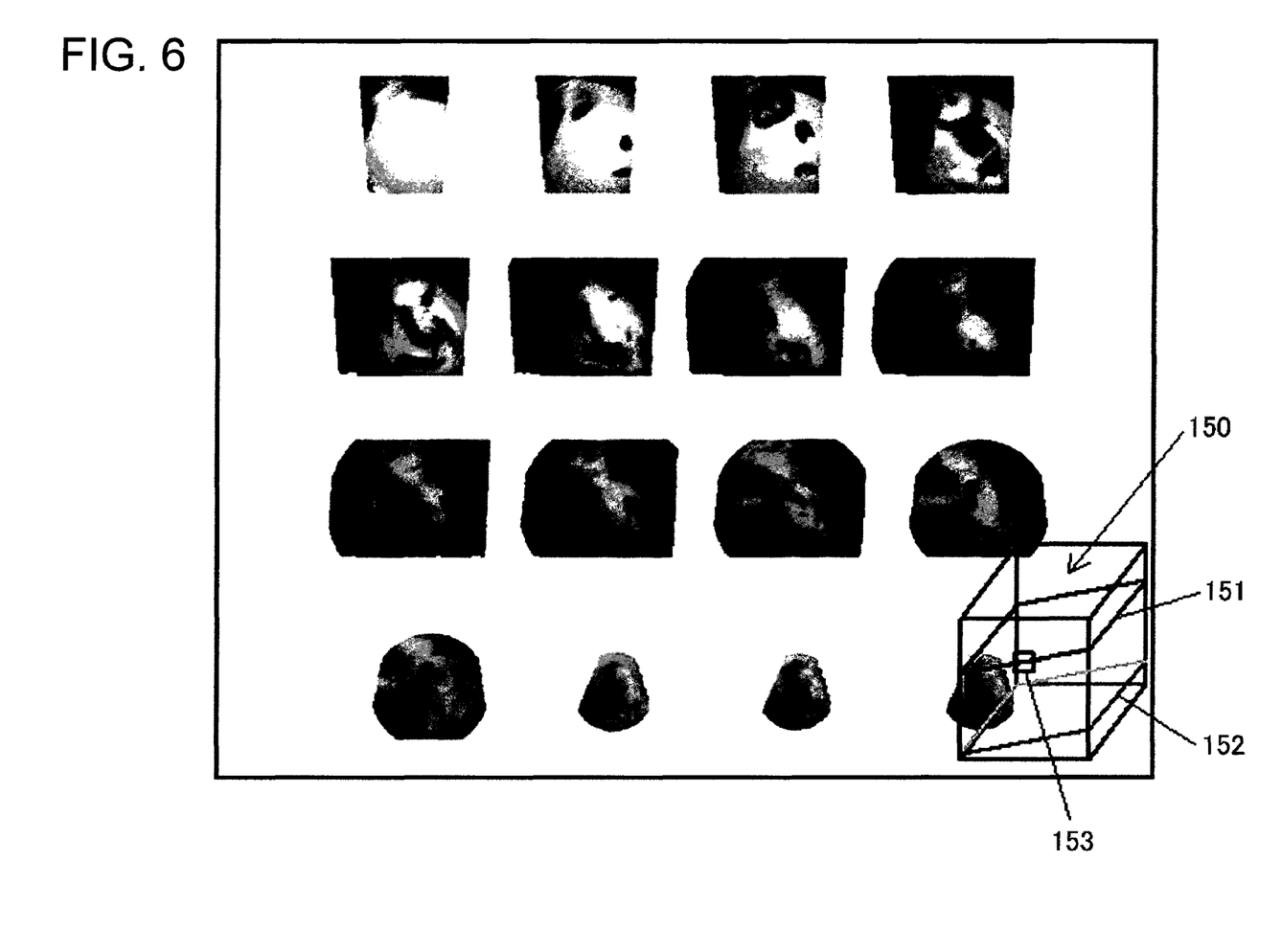
[FIG. 6] is a view showing one example of the multi-slice display.

The multi-slice display is the display method that arranges and displays sections after the three-dimensional image is cut at any plurality of positions (on the same flat surface), as shown in FIG. 5 and FIG. 6. FIG. 5 shows an example of 9 divided images, and FIG. 6 shows an example of 16 divided images.

The position to be division-displayed can be arbitrarily set by an operator from a trackball, a keyboard and the like, or can be based on a preset condition.

In this way, by displaying an arbitrary cross-section, it is now possible to draw the interior of an object whose other shape could only be observed by a three-dimensional image.

In FIG. 5, a slice position display FIG. 150 is a figure that specifies the range over which the three-dimensional image is divided and displayed, and displays which position is divided and displayed, and a slice upper limit line 151 and a slice lower limit line 152 indicate an upper limit position and a lower limit position at which the three-dimensional image is cut (sliced), respectively, and display the position to where the three-dimensional image is sliced.

In FIG. 5, the slice upper limit line 151 and the slice lower limit line 152 are set in parallel in upper and lower directions. However, they can be inclined and set as shown in FIG. 6.

Also, in accordance with the two motor angle information of the rotation and the oscillation that are detected by the angle detecting circuit 121 for generating the angle information of the high resolution from the two encoder signals of the rotation and the oscillation, the number of the division images and the directions are optimized, and the division display process is carried out.

In this way, the slice upper limit line 151 and the slice lower limit line 152 can be arbitrarily set, and the manner of setting it will be described below.

When a multi-slice display mode is set by the operation of a user, a slice upper limit and a slice lower limit of default are firstly set, and the sections divided by the division number between them are displayed.

Next, when entering an inclination setting mode for setting an inclination, as shown in FIG. 6, a selection mark 153 is displayed on the side in front of the slice upper limit line 151, and the side on which this selection mark 153 is displayed can be moved upwardly and downwardly by the moving device such as the trackball or the like. Then, when a key to move the selection mark 153 is pushed, the selection mark 153 is moved to an adjacent side. Then, the side to which the selection mark 153 is moved can be moved upwardly and downwardly.

Then, When entering a position setting mode, the selection mark 153 is moved to the slice lower limit line 152 that is displayed at the same inclination as the above-set slice upper limit line 151. Thus, the whole of the slice lower limit line 152 can be moved upwardly and downwardly.

Executing such an operation can set the upper limit and the lower limit when the three-dimensional image is slice-displayed and its angle.

Here, in the case that the upper limit and the lower limit are set and the division display number is, for example, the 16-division, as shown in FIG. 6, since it is regularly divided by 16 from the upper limit to the lower limit and displayed, the regularly divided multi-slice display can be attained.

At the time of the division, it can be divided not only in the regular manner, but also in the manner that it is divided gradually widely from the upper direction or gradually narrowly, or in the manner that the central portion is finely divided and the upper and lower portions are roughly divided.

Even in the case that the upper limit and the lower limit and its angle are changed as mentioned above, by operating a reset function from a menu or the like, it is possible to return to the setting of the default.

Those operations can be attained, because the three-dimensional data stored in the image memory 114 can be read at any position by the high speed operation processing circuit 122 and this control is carried out by the host up 117.

Figure 7:
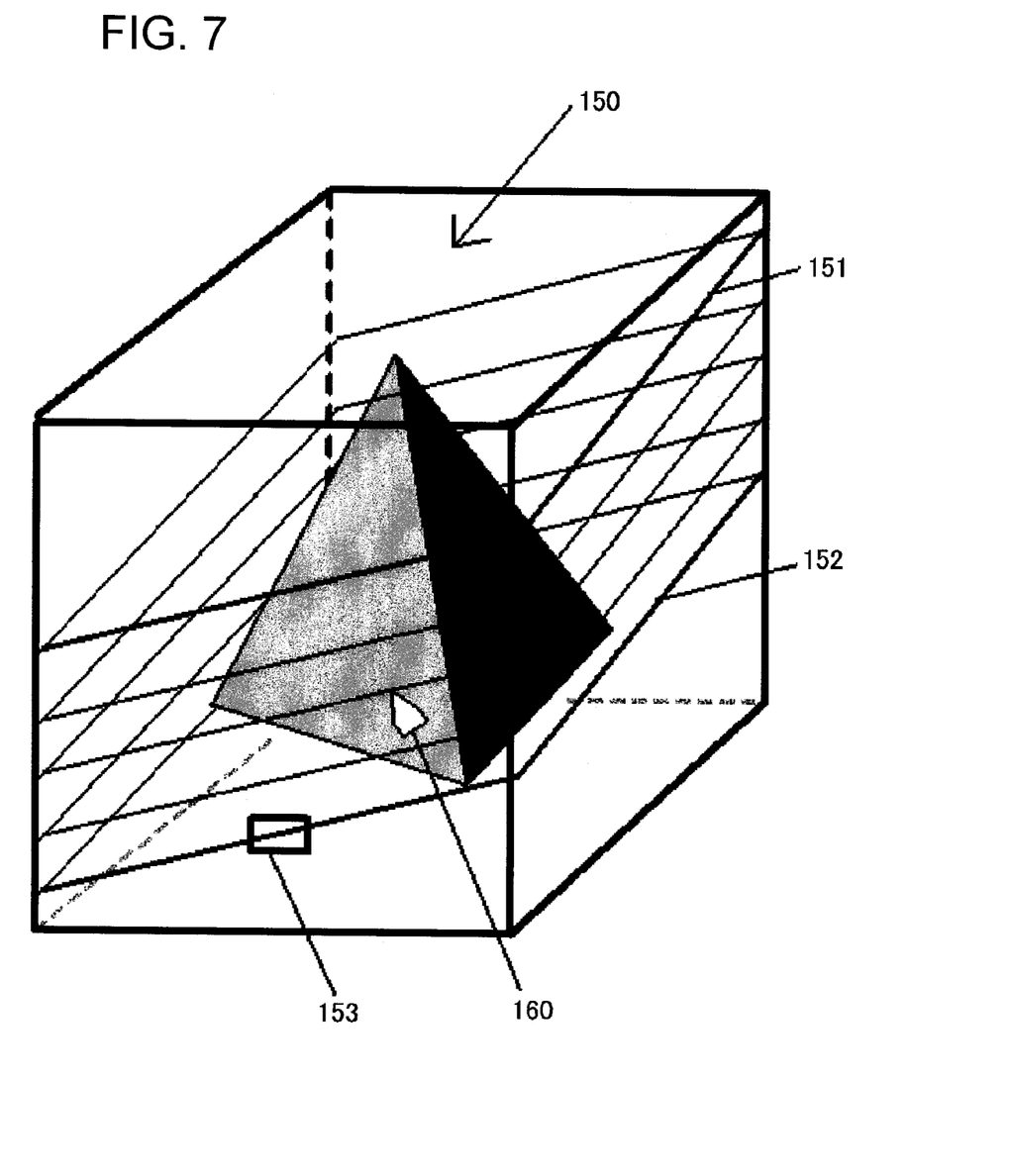
[FIG. 7] is a view showing one example of a division position in the multi-slice display.

The display examples in FIG. 5 and FIG. 6 display that the slice position display figure 150 is only the frame of the outer circumference. However, as shown in FIG. 7, if the three-dimensional image is displayed inside this slice position display figure 150 and further the slice upper limit line 151 and the slice lower limit line 152 are displayed, which portion of the three-dimensional image is divided can be easily grasped.

Figure 8:
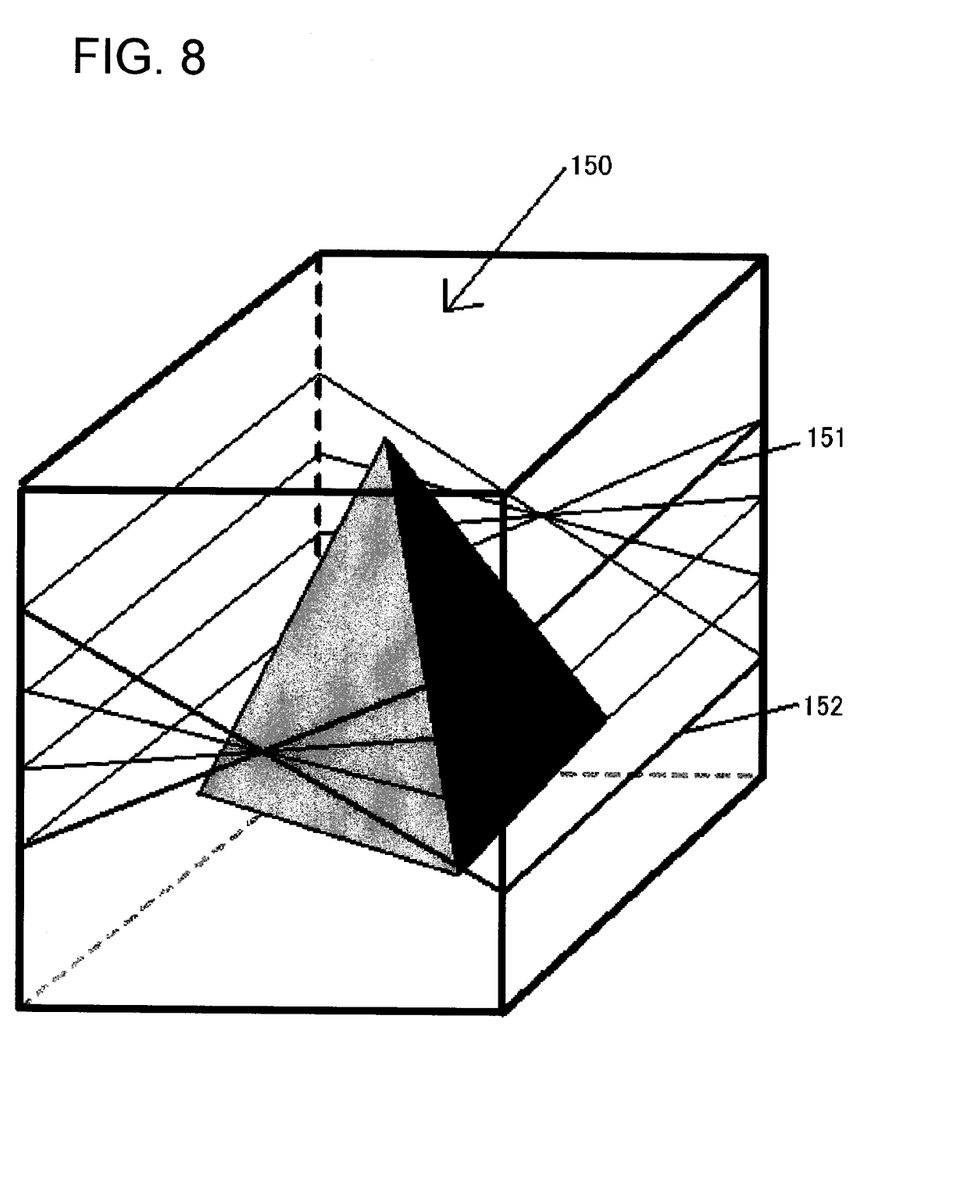
[FIG. 8] is a view showing one example of the division position in the multi-slice display.
Figure 9:
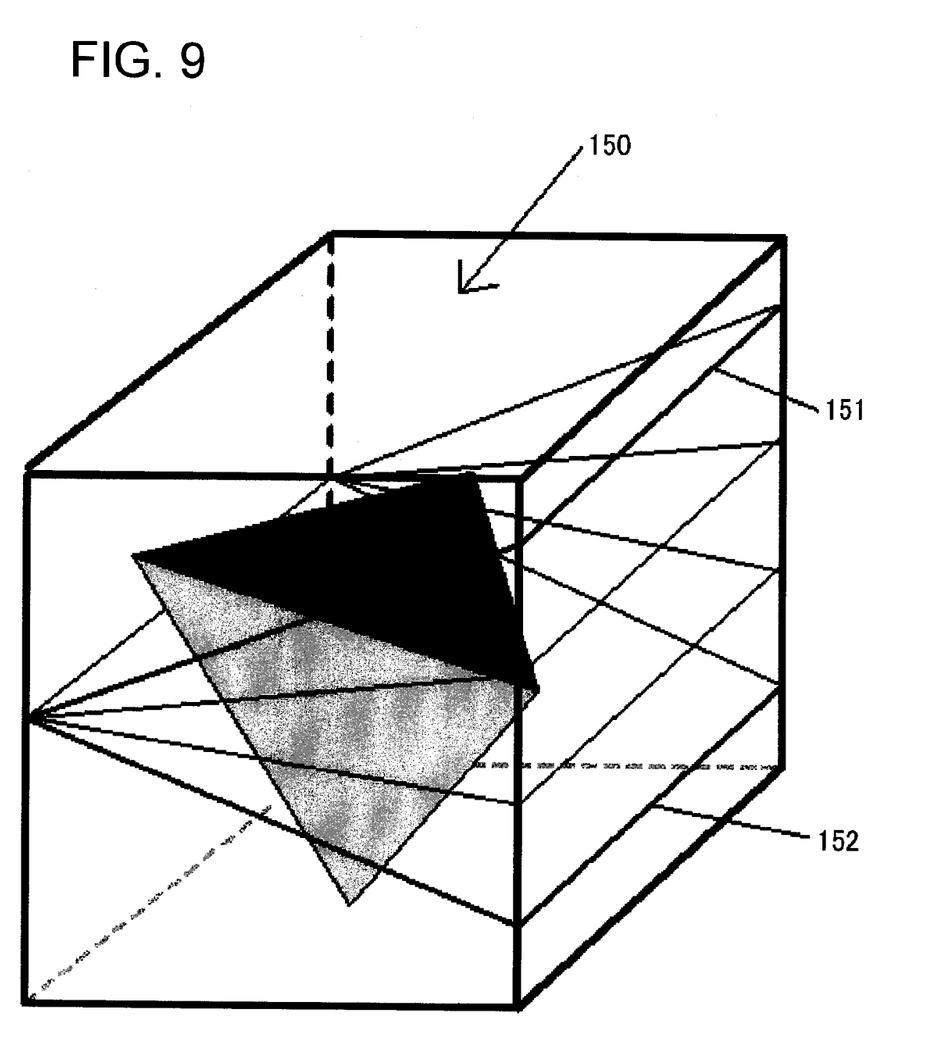
[FIG. 9] is a view showing one example of the division position in the multi-slice display.

Also, the dividing slicing method can carry out not only the above-mentioned parallel slice, but also the division slice with one point as a center, or the division slice to a fan shape, as shown in FIG. 8 and FIG. 9.

For the purpose of the easy understanding of the correspondence between the divided slice images and the division lines indicated on the slice position display figure 150, the respective slice images are surrounded with lines. Then, the colors of those surrounding lines and division lines and line kinds are made coincident and displayed. Consequently, the correspondence between the slice positions and the slice images are easily understood.

Also, the three-dimensional image can be arbitrarily rotated or moved as shown in FIG. 9. Thus, by rotating or moving the three-dimensional image inside the slice position display figure 150, it is possible to arbitrarily change the portion to be sliced.

Also, while the data are sequentially stored into the image memory 114, the three-dimensional processing unit 120 forms the three-dimensional image. Consequently, the three-dimensional image can be displayed at real time, namely, the three-dimensional image can be displayed as a so-called dynamic image. Thus, the simultaneous display of the real time three-dimensional image display and the multi-slice display that cannot be attained in CT or MRI becomes possible.

Also, as the three-dimensional image is updated at real time, the multi-slice display can be updated at a constant interval.

As explained above, as for the three-dimensional dynamic image that is sequentially updated at real time, the tomographic image is division-displayed at any position. Consequently, together with the three-dimensional dynamic image that cannot be attained in CT or MRI, the situation inside a diagnosis target can be expanded and observed. Thus, the precision and efficiency of the diagnosis can be greatly improved. Also, a so-called enlargement diagnosis, which observes and diagnoses the portion to be observed and its periphery at the same time, can be easily executed.

The operation of the enlargement display of the divided slice image will be described below.

Figure 10:
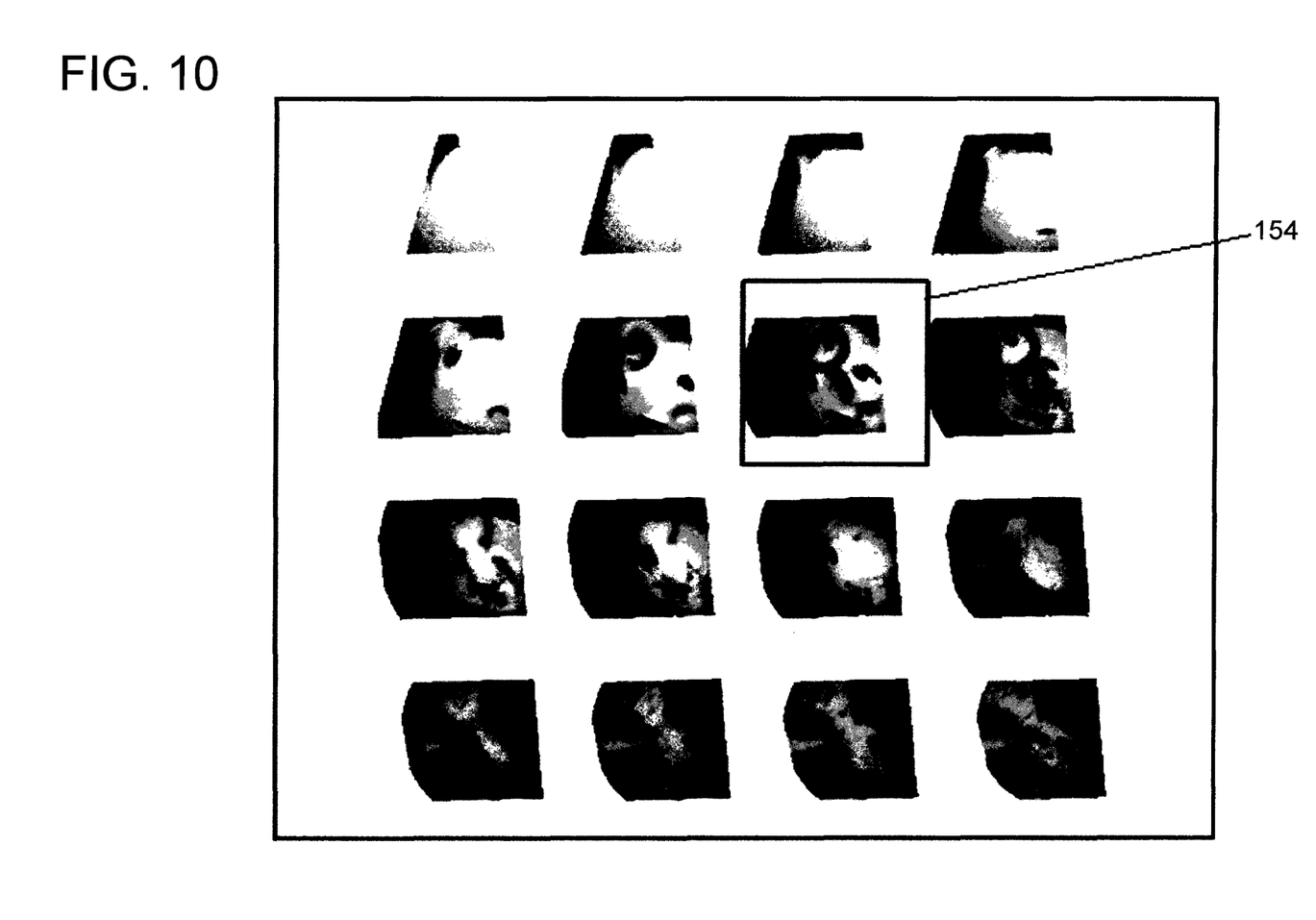
[FIG. 10] is a view when one image is selected in the multi-slice display.
Figure 11:
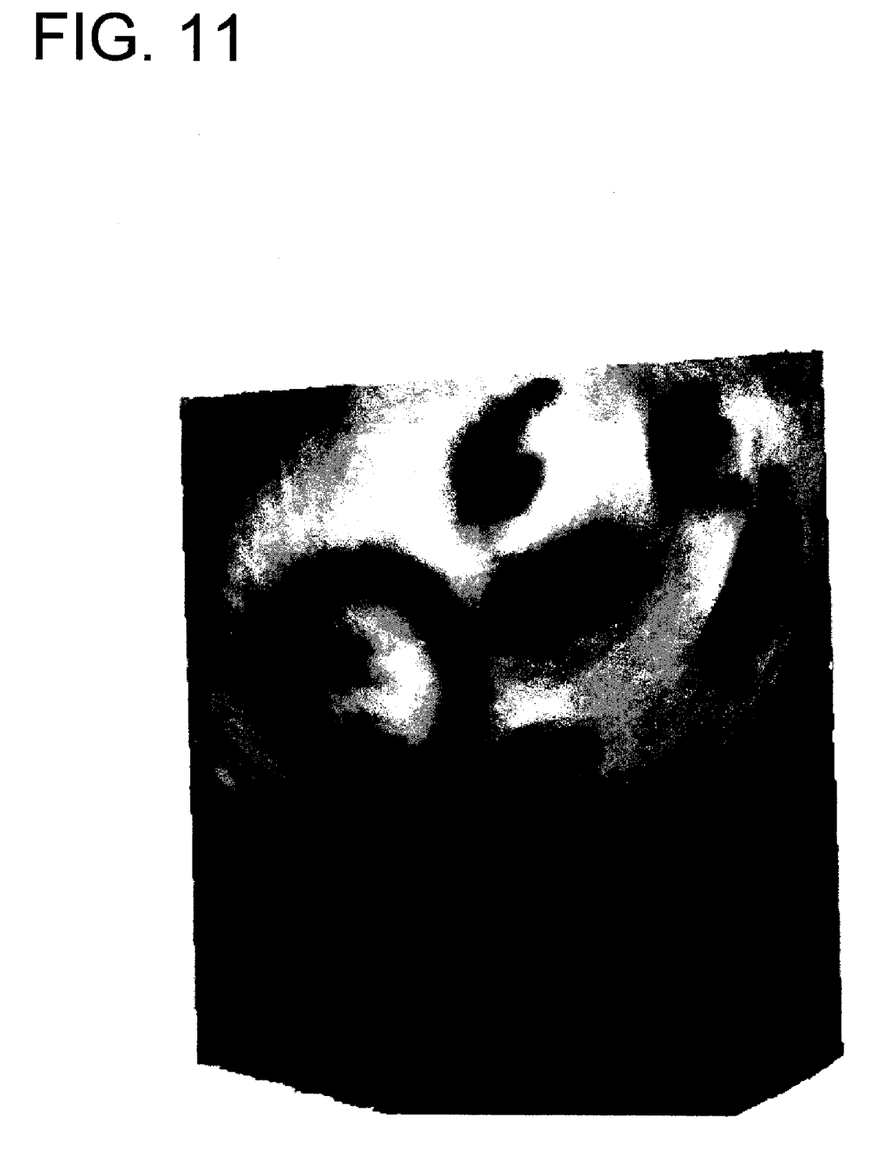
[FIG. 11] is an enlargement view of the image selected in the multi-slice display.

As shown in FIG. 10, when any image that is division-displayed (in FIG. 10, a selection image 154) is selected by using the trackball or the like and a key for a determination is pushed, its selected image is enlargement-displayed as shown in FIG. 11. Moreover, when the key for the determination is again pushed in the enlargement display state, the operation returns to the division display.

Also, a pointer 160 shown in FIG. 7 is mated to the division line on the three-dimensional image and then the key for the determination is pushed, the tomographic image of its division line portion can be enlargement-displayed.

With such operations, any division image can be enlargement-displayed and evaluated in detail. Also, it is possible to easily return to the division display and then select a different image, which enables the great improvement of the precision and efficiency of the diagnosis.

Also, since by using the pointer 160, the division line on the three-dimensional image display is selected on the screen, the slice image only at the necessary position can be displayed.

In this embodiment, the configuration in which the ultrasonic transducer unit is rotated and oscillated to consequently form the three-dimensional image is described. However, the configuration in which an array probe where the ultrasonic transducer units are arranged in the shape of an array is oscillated to consequently create the three-dimensional image, or a two-dimensional array probe in which ultrasonic probes are two-dimensionally arranged can carry out the similar display. Thus, the precision and efficiency of the diagnosis can be greatly improved.

When the mechanical sector probe is used, the ultrasonic transducer units are not required to be arranged on the array. Thus, the tip of the probe can be made smaller. Also, even the image just beside the probe (in a 180-degree direction) can be drawn without any distortion. Thus, this is effective in the diagnosis especially in the insertion into the body.

Also, when the array probe is used, focus can be applied to the ultrasonic wave to be transmitted and received. Thus, a distance resolution and an orientation resolution can be improved.

Even if any probe is used, according to the present invention, the tomographic image in which the three-dimensional image is arbitrarily divided can be displayed. Thus, when the different probes are used for different usage fields, the diagnosis precision can be further improved.

INDUSTRIAL APPLICABILITY

As described above, the ultrasonic diagnosing apparatus and the ultrasonic image display method, according to the present invention, display the three-dimensional image at real time, and further division-display any tomographic images of this three-dimensional image at any angle, direction and division number, and consequently have the effect that the improvement of the diagnosis precision can be attained, and they are effective as the ultrasonic diagnosing apparatus and the like that can display the plurality of tomographic images together with the three-dimensional image display.

The invention claimed is:

1. An ultrasonic diagnosing apparatus, comprising:
   connecting means for connecting a probe having an ultrasonic transducer unit to transmit and receive ultrasonic waves;
   transmitting/receiving means for supplying an ultrasonic signal to said ultrasonic transducer unit and carrying out a reception process of the ultrasonic signal received by said ultrasonic transducer unit;
   an image memory for storing said received and processed ultrasonic signal as an image data; and
   three-dimensional operating means for forming a three-dimensional image from the image data stored in said image memory at real time, said three-dimensional operating means including an operation processing circuit for carrying out processes of generation, treatment and cut of the three-dimensional image data,
   wherein said three-dimensional operating means is designed so as to cut and division-display a set number of tomographic images of said three-dimensional image by performing cutting at a set angle within a three-dimensional display range including said three-dimensional image, and between a position of a slice upper limit and a position of a slice lower limit of a range of an intended division display so as to display said set number of tomographic images, wherein the displayed set number of tomographic images includes a plurality of different slice images automatically cut from between the position of the slice upper limit and the position of the slice lower limit, and further wherein the position of the slice upper limit and the position of the slice lower limit are moveable relative to the three-dimensional display range to set the set angle within the three-dimensional display range at which cutting is performed.

2. The ultrasonic diagnosing apparatus according to claim 1, comprising means for selecting said division-displayed tomographic image, wherein said selected tomographic image is designed to be enlargement-displayed.

3. The ultrasonic diagnosing apparatus according to claim 1, comprising means for selecting the position of the tomographic image displayed on said three-dimensional image, wherein the tomographic image of said selected position is designed to be enlargement-displayed.

4. The ultrasonic diagnosing apparatus according to claim 1, wherein said three-dimensional operating means is designed to cut said set number of tomographic images at a preliminarily specified interval.

5. The ultrasonic diagnosing apparatus according to claim 1, wherein said three-dimensional operating means is designed to cut said set number of tomographic images in a manner that said range of said intended division display is divided gradually widely from said slice upper limit or gradually narrowly.

6. The ultrasonic diagnosing apparatus according to claim 1, wherein said three-dimensional operating means is designed to cut said set number of tomographic images in a manner that the central portion of said range of said intended division display is finely divided and the upper and lower portions close to said slice upper limit and said slice lower limit respectively are roughly divided.

7. An ultrasonic diagnosing apparatus, comprising:
connecting means for connecting a probe having an ultrasonic transducer unit to transmit and receive ultrasonic waves, a rotating motor and an oscillating motor;
transmitting/receiving means for supplying an ultrasonic signal to said ultrasonic transducer unit and carrying out a reception process of the ultrasonic signal received by said ultrasonic transducer unit;
rotation control means for carrying out a rotation control of said rotating motor;
oscillating control means for carrying out an oscillating control of said oscillating motor;
an image memory for storing said received and processed ultrasonic signal as an image data; and
three-dimensional operating means for forming a three-dimensional image from the image data stored in said image memory, said three-dimensional operating means including an operation processing circuit for carrying out processes of generation, treatment and cut of the three-dimensional image data,
wherein said three-dimensional operating means is designed so as to cut and division-display a set number of tomographic images of said three-dimensional image by performing cutting at a set angle within a three-dimensional display range including said three-dimensional image, and between a position of a slice upper limit and a position of a slice lower limit of a range of an intended division display so as to display said set number of tomographic images, wherein the displayed set number of tomographic images includes a plurality of different slice images automatically cut from between the position of the slice upper limit and the position of the slice lower limit, and further wherein the position of the slice upper limit and the position of the slice lower limit are moveable relative to the three-dimensional display range to set the set angle within the three-dimensional display range at which cutting is performed.

8. The ultrasonic diagnosing apparatus according to claim 7, comprising means for selecting said division-displayed tomographic image, wherein said selected tomographic image is designed to be enlargement-displayed.

9. The ultrasonic diagnosing apparatus according to claim 7, comprising means for selecting the position of the tomographic image displayed on said three-dimensional image, wherein the tomographic image of said selected position is designed to be enlargement-displayed.

10. The ultrasonic diagnosing apparatus according to claim 7, wherein said three-dimensional operating means is designed to cut said set number of tomographic images at a preliminarily specified interval.

11. The ultrasonic diagnosing apparatus according to claim 7, wherein said three-dimensional operating means is designed to cut said set number of tomographic images in a manner that said range of said intended division display is divided gradually widely from said slice upper limit or gradually narrowly.

12. The ultrasonic diagnosing apparatus according to claim 7, wherein said three-dimensional operating means is designed to cut said set number of tomographic images in a manner that the central portion of said range of said intended division display is finely divided and the upper and lower portions close to said slice upper limit and said slice lower limit respectively are roughly divided.

13. An ultrasonic image display method comprising the steps of:
receiving an ultrasonic signal from a probe having an ultrasonic transducer unit;
storing the received ultrasonic signal as an image data in an image memory;
forming a three-dimensional image from the image data stored in said image memory using an operation processing circuit for carrying out processes of generation, treatment and cut of the three-dimensional image data;
setting, by a user, a number of tomographic images to be cut;
setting, by the user, a slice upper limit position;
setting, by the user, a slice lower limit position;
setting, by the user, a slice angle; and
cutting and division-displaying said set number of tomographic images of said three-dimensional image by performing cutting at said set angle within a three-dimensional display range including said three-dimensional image, and between the slice upper limit position and the slice lower limit position so as to display said set number of tomographic images, wherein the displayed set number of tomographic images includes a plurality of different slice images that are automatically cut from between the slice upper limit position and the slice lower limit position, and further wherein the step of setting, by the user, a slice angle includes moving the slice upper limit position and the slice lower limit position relative to the three-dimensional display range.

* * * * *